US012629040B2

(12) United States Patent
Pfeiffer et al.

(10) Patent No.: US 12,629,040 B2
(45) Date of Patent: *May 19, 2026

(54) BLOOD PRESSURE MEASURING SYSTEM COMPRISING A KINKING-PROOF SHELL

(71) Applicant: PHILIPS MEDIZIN SYSTEME BÖBLINGEN GMBH, Böblingen (DE)

(72) Inventors: Ulrich Pfeiffer, Munich (DE); Sabastian Kisban, Munich (DE); Tobias Thomamüller, Bruckmuhl (DE); Anna-Luisa Uhlitz, Munich (DE); Reinhold Knoll, Neuburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 754 days.

This patent is subject to a terminal disclaimer.

(21) Appl. No.: 17/735,534

(22) Filed: May 3, 2022

(65) Prior Publication Data

US 2022/0257130 A1 Aug. 18, 2022

Related U.S. Application Data

(63) Continuation of application No. 14/763,586, filed as application No. PCT/EP2014/000340 on Feb. 7, 2014, now Pat. No. 11,317,819.

(30) Foreign Application Priority Data

Feb. 8, 2013 (WO) .......................... EP2013/000386

(51) Int. Cl.
*A61B 5/022* (2006.01)

(52) U.S. Cl.
CPC ................................ *A61B 5/02233* (2013.01)

(58) Field of Classification Search
CPC ..... A61B 5/021; A61B 5/022; A61B 5/02225; A61B 5/0225; A61B 5/02255; A61B 5/02233

See application file for complete search history.

(56) References Cited

U.S. PATENT DOCUMENTS 4,501,280 A 2/1985 Hood
5,394,563 A 3/1995 Doyle
(Continued)

FOREIGN PATENT DOCUMENTS

CN 1692876 A 11/2005
CN 102008298 A 4/2011
(Continued)

OTHER PUBLICATIONS

International Search Report & Written Opinion, International Application No. PCT/EP2014/000340, Mailed Jun. 5, 2014.

*Primary Examiner* — Jacqueline Cheng
*Assistant Examiner* — Tho Q Tran
(74) *Attorney, Agent, or Firm* — Brynne J. Corcoran

(57) ABSTRACT

The present invention refers to a blood pressure measuring system (10) configured to surround a patient's body part (E), comprising pressurization means (12, 14) for applying pressure to the body part (E), and comprising a kinking-proof shell (20; 30), wherein the kinking-proof shell (20; 30) is arranged so as to be located between the pressurization means (12, 14) and the body part (E), when the blood pressure measuring system (10) surrounds the body part (E). The present invention further refers to a method of applying a blood pressure measuring system (10).

19 Claims, 10 Drawing Sheets

(56)  References Cited

U.S. PATENT DOCUMENTS

| | | |
|---|---|---|
| 6,620,116 B2 | 9/2003 | Lewis |
| 7,153,270 B2 | 12/2006 | Sano |
| 8,998,817 B2 | 4/2015 | Pfeiffer |
| 2001/0001188 A1 | 5/2001 | Avner |
| 2001/0005777 A1 | 6/2001 | Nakagawa |
| 2002/0026121 A1 | 2/2002 | Kan |
| 2005/0015015 A1 | 1/2005 | Mizukoshi |
| 2005/0171445 A1 | 8/2005 | Millay |
| 2005/0182332 A1 | 8/2005 | Sano |
| 2006/0224069 A1 | 10/2006 | Sano |
| 2007/0203416 A1* | 8/2007 | Lowe ................. A61B 5/02233<br>600/485 |
| 2009/0062688 A1 | 3/2009 | Todokoro |
| 2009/0234381 A1 | 9/2009 | Karo |
| 2009/0312651 A1* | 12/2009 | Sano ................. A61B 5/02141<br>600/493 |
| 2010/0106029 A1* | 4/2010 | Fraden ............... A61B 5/02208<br>600/490 |
| 2010/0106031 A1 | 4/2010 | Souma |
| 2010/0137725 A1 | 6/2010 | Takahashi |
| 2011/0054330 A1 | 3/2011 | Pfeiffer |
| 2011/0112412 A1 | 5/2011 | Sano |
| 2012/0240377 A1 | 9/2012 | Ashida |
| 2012/0253210 A1 | 10/2012 | Uesaka |
| 2012/0265240 A1 | 10/2012 | Ganske |
| 2012/0302901 A1 | 11/2012 | Kobayashi |
| 2013/0123649 A1 | 5/2013 | Mcculloch |

FOREIGN PATENT DOCUMENTS

| | | |
|---|---|---|
| CN | 102688026 A | 9/2012 |
| DE | 102009039257 A1 | 3/2011 |
| JP | 09117418 A | 5/1997 |
| JP | 2000051158 A | 2/2000 |
| JP | 2004159967 A | 6/2004 |
| JP | 2005230175 A | 9/2005 |
| JP | 2009072548 A | 4/2009 |
| JP | 2010522610 A | 7/2010 |
| JP | 2013502940 A | 1/2013 |

* cited by examiner

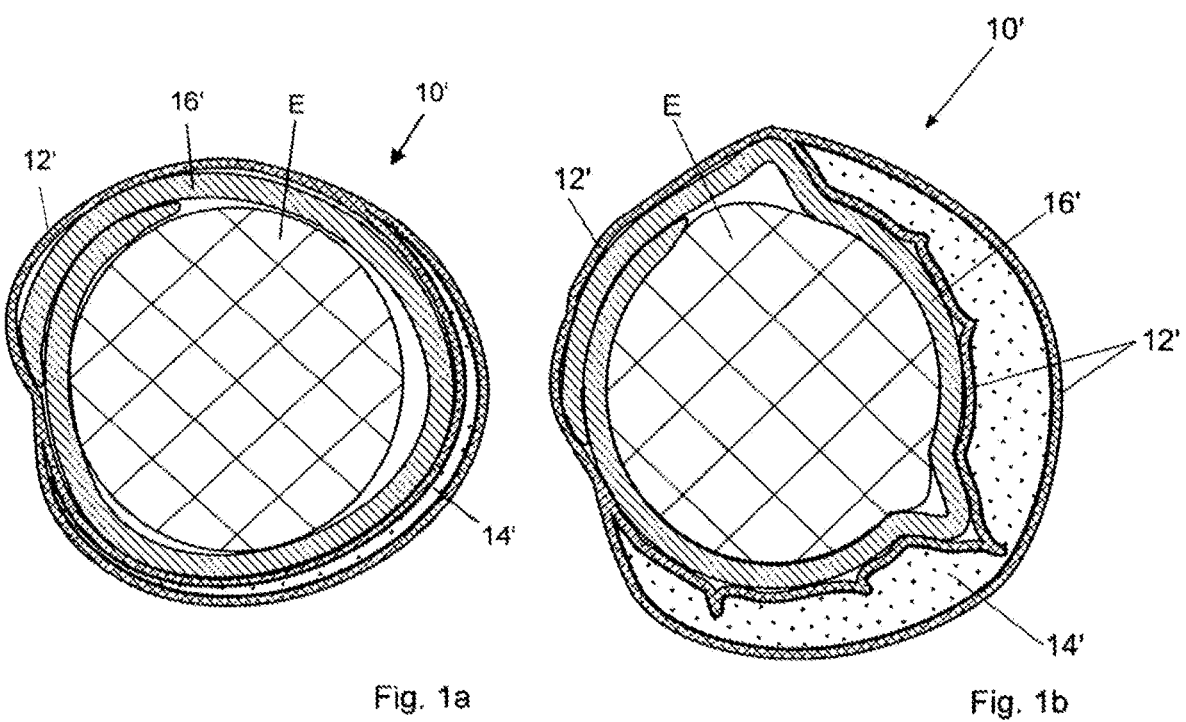
Fig. 1a                    Fig. 1b
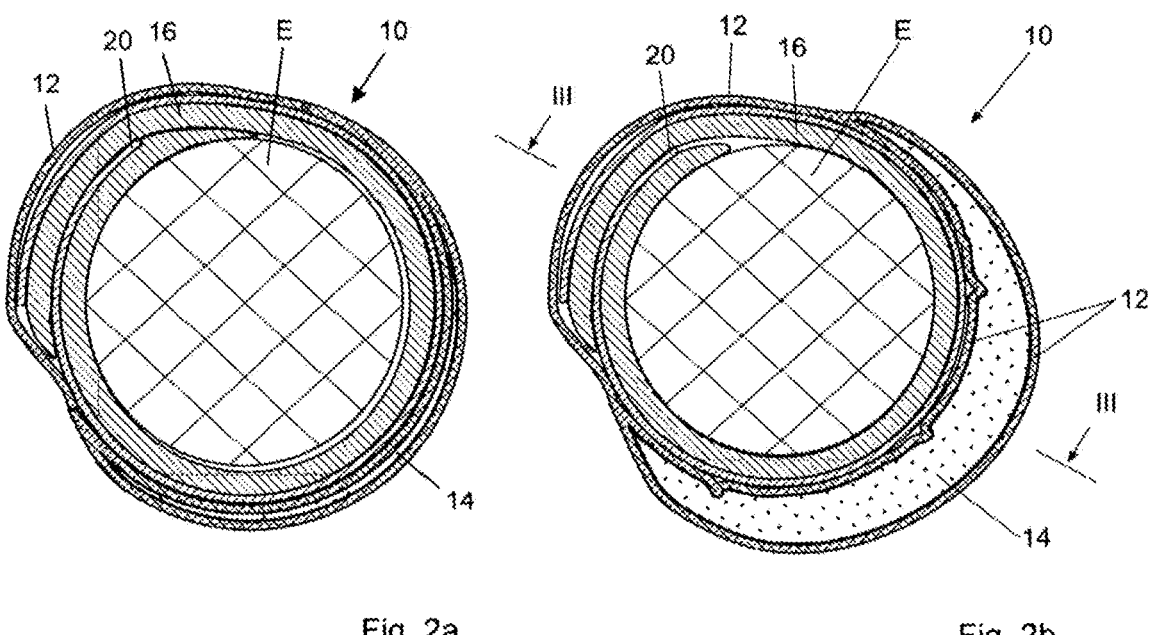
Fig. 2a                    Fig. 2b

BLOOD PRESSURE MEASURING SYSTEM COMPRISING A KINKING-PROOF SHELL

CROSS REFERENCE TO RELATED APPLICATION

The present application is a continuation of co-pending U.S. patent application Ser. No. 14/763,586, filed Feb. 7, 2014, which is the U.S. National Phase application under 35 U.S.C. § 371 of International Application No. PCT/EP2014/000340 filed Feb. 14, 2014, which claims the benefit of International Application No. PCT/EP2013/000386 filed Feb. 8, 2013. These applications are hereby incorporated by reference herein.

The invention refers to a blood pressure measuring system configured to surround a patient's body part, usually an extremity, comprising pressurization means for applying pressure to the body part, and comprising a kinking-proof shell. The present invention further refers to a method of applying a blood pressure measuring system.

Such blood pressure measuring systems are generally known in the art. For example the company OMRON offers such a system, named "Comfort Cuff" (PZN 28861 14). The "Comfort Cuff" product is adapted to be positioned around a patient's upper arm. In order to apply pressure to the patient's upper arm for non-invasively measuring the patient's arterial blood pressure, the "Comfort Cuff" comprises a pressure cuff that can be inflated by supplying air to a fluid bag of the pressure cuff. A pressure sensor measures the pressure in the fluid bag via a hose line. It is assumed that the pressure in the fluid bag substantially corresponds to the pressure of the body tissue at an outer surface of the patient's upper arm. Furthermore, the "Comfort Cuff" comprises a relatively rigid (and thus kinking-proof) outer shell of substantially cylindrical shape, exteriorly surrounding the pressure cuff with the fluid bag. The outer shell makes it more comfortable to apply the "Comfort Cuff" to the patient's upper arm, because it is not necessary to wrap the pressure cuff around the arm. Moreover, the required filling volume of the fluid bag can be reduced compared to blood pressure measuring systems without such a shell. Furthermore, the process of positioning the system around the patient's upper arm and of measuring the patient's blood pressure also becomes better reproducible with such a shell.

The blood pressure measuring system described above has a problem that wrinkles (or kinks) may be formed at a compression acting surface of the fluid bag when measuring the blood pressure. If wrinkles are formed at the compression acting surface of the fluid bag, part of the patient's tissue at the measuring site may be trapped in the valley portions of the wrinkles, which may cause slight subcutaneous bleeding at the measuring site. Furthermore, wrinkles negatively influence the amplitude, form and reproducibility of the measured signal.

To avoid subcutaneous bleeding at the measuring site, i.e. at the skin of the patient's upper arm, when using a blood pressure measuring system as described above, US 2010/0137725 A1 proposes to accommodate a cushion material between the compression acting surface of the fluid bag and the measuring site. To ensure that, instead of the skin, the cushion material is trapped in the valley portions of the wrinkles, the cushion material has to be of a relatively high compressibility.

However, accommodating a cushion material between the compression acting surface of the fluid bag and the measuring site does not avoid the negative influence of the wrinkles (or kinks) as to the amplitude, form and reproducibility of the measured signal. To the contrary, part of the arterial pressure is absorbed and attenuated by the cushion material, thus, negatively influencing the measurement accuracy. As one countermeasure for preventing lowering in the measurement accuracy by pressure propagation loss, US 2010/0137725 A1 proposes to apply an empirical approach, i.e. to calculate for example the diastolic pressure value based on the measured maximum pressure value multiplied by an empirically determined factor. However, such empirically approaches are per se of poor preciseness, leading to unsatisfying results.

It is therefore an object of the present invention to improve blood pressure measuring systems of the above type, especially in order to avoid subcutaneous bleeding at the measuring site, in particular to improve the measurement accuracy.

This object is achieved by the features of independent claim 1. Preferred features of the inventive system are described in the dependent claims. In particular, the object is achieved by a blood pressure measuring system configured to surround a patient's body part, comprising pressurization means for applying pressure to the body part, and comprising a kin king-proof shell, wherein the kinking-proof shell is arranged so as to be located between the pressurization means and the body part, when the blood pressure measuring system surrounds the body part.

In contrast to the known blood pressure measuring systems described above, the blood pressure measuring system according to the present invention does not have the kinking-proof shell radially outside of the fluid bag (the fluid bag serving as the pressurization means to apply pressure to the patient's body part) but the kinking-proof shell is located (or sandwiched) between the pressurization means (e.g. comprising a pressure actuator, especially in conjunction with a fluid bag) and the body part, when the blood pressure measuring system surrounds the body part for measuring the patient's blood pressure. Therefore, the kinking-proof shell—that is relatively stiff—avoids or at least significantly reduces the creation of wrinkles or kinks at the compression acting surface of the fluid bag. Consequently, the measurement accuracy can be improved, since no wrinkles negatively influence the amplitude, form and reproducibility of the measured signal. In particular, if a pressure sensor unit is located at least partially between the kinking-proof shell and the body part, a high accuracy of the signals measured by the pressure sensor unit can be achieved. With such a configuration of the pressure sensor unit, the kinking-proof shell does not absorb or attenuate the arterial pressure signal.

In particular, the present invention is also based on the finding that the kinking-proof shell may provide sufficient stiffness of the blood pressure measuring system during measurement. In fact, it has been found that, according to one preferred embodiment, a required stiffness of the blood pressure measuring system may be ensured exclusively by the kinking-proof shell.

By arranging the kinking-proof shell according to the present invention, the pressurization means, e.g. a pressure actuator with a fluid bag, maintains in its substantially ring-shaped form (without any wrinkles) when pressure is applied to the body part. Also, an optional (additional) flexible element having a stiffening element for stiffening the flexible element may provide stiffness, if such a flexible element is accommodated between the kinking-proof shell and patient's body part, as will be described in more detail below. But, such an optional (additional) flexible element is not necessarily required in order to ensure sufficient stiffness, as will be described in detail below.

When pressure is applied to the body part by the pressurization means, overlapping portions of the kinking-proof shell may move or slide relatively to each other, thereby reducing the diameter of the kinking-proof shell.

The kinking-proof shell according to the present invention preferably exhibits a stiffness notably larger than the stiffness of the flexible wall of a fluid bag if the pressurization means comprise such a fluid bag. Preferably, the stiffness of the kinking-proof shell is chosen so as to ensure that no buckling of the kinking-proof shell will occur when pressure is applied to the body part by the pressurization means for measuring the patient's blood pressure. At the same time, the kinking-proof shell should be flexible enough so as to allow the kinking-proof shell to reduce its inner diameter when pressure is applied to the fluid bag for measuring the patient's blood pressure.

In case an optional (additional) flexible element having a stiffening element is accommodated between the kinking-proof shell and patient's body part, the stiffness of the kinking-proof shell is preferably also larger than the stiffness of the flexible element, at least as long as the flexible element is not stiffened by the stiffening element.

Similarly to the outer shell of the "Comfort Cuff" product, the kinking-proof shell accommodated according to the present invention can provide more comfort in view of the positioning of the blood pressure measuring system around the patient's body part, such as the patient's upper arm or leg, compared to a conventional blood pressure cuff without a shell, because it is not necessary to wrap a pressure cuff around the arm. Moreover, the required filling volume of a fluid bag can be reduced compared to blood pressure measuring systems without a corresponding shell. Furthermore, by means of the shell, the process of positioning the system around the patient's upper arm and of measuring the patient's blood pressure is reproducible more reliably.

The pressurization means may be implemented by a mechanical pressure actuator, in particular by a fluid-free pressure actuator, such as a pressure cuff comprising an actuator, e.g. a motor, and a cable pull. The cable of the cable pull may connect the two longitudinal ends of the pressure cuff and/or the cable may surround the body part. However, additionally or alternatively to a mechanical pressure actuator, the pressurization means may equally comprise a pressure actuator with a fluid bag, similar to the above described "Comfort Cuff" product.

If the pressurization means comprise a pressure actuator with a fluid bag, another advantage of accommodating the kinking-proof shell according to the invention, i.e. accommodating the kinking-proof shell between the pressure actuator with the fluid bag and the body part, is that more pressure (e.g. the 1,5-fold amount of pressure) has to be applied to the fluid bag for achieving the same pressure at the patient's body part compared to a system of the prior art, because part of the applied pressure is not transmitted to the patient's body part due to the relatively rigid kinking-proof shell. Applying more pressure to the fluid bag may result in making the fluid bag—which acts as a gas spring—more rigid or inflexible and making the system stiffer, thereby reducing attenuation of pressure oscillations stemming from the patient's heart beats. Thus, measurement accuracy can be further improved.

Notably, with the blood pressure measuring system according to the present invention, another relatively rigid shell may additionally be applied radially outside from the pressurization means, similar to the outer shell of the above described "Comfort Cuff" product. Such a configuration allows reducing the required filling volume of a fluid bag— if the pressurization means comprises a pressure actuator with a fluid bag—when the fluid bag is sandwiched between the radially outer rigid shell and the radially inner kinking-proof shell. Reducing the filling volume, in turn, allows for faster reaching the required pressure to be applied to the patient's body part.

Preferably, the kinking-proof shell is a stiffening component which is configured for ensuring stiffness of the blood pressure measuring system for pressure measurement, especially by interaction with the pressurization means. The kinking-proof shell may be the sole stiffening component of the system, the stiffening component exhibiting a structural solidity or strength and being configured for providing stiffness for or during pressure measurement. The pressurization means do not have to provide any stiffening element. Also, the system does not have to exhibit any further stiffening element at all. In other words: The kinking-proof shell is a stiffening component which is configured such that the stiffness of the blood pressure measuring system can be ensured exclusively by the kinking-proof shell, especially by interaction with the pressurization means. Thus, the present invention is also based on the concept that any stiffening function may be provided by the kinking-proof shell. There is no need for applying any vacuum in order to stiffen any flexible element. There is no need for any evacuation means. As evacuation of any cavity or any additional stiffening element is not necessarily required, the system also allows for easy and fast application.

Also, by providing the kinking-proof shell as a stiffening component, it may be more practicable to provide the blood measurement system as a disposable. A stiffening kinking-proof shell allows for reducing the number of components, providing a cost-effective system.

Preferably, the kinking-proof shell is configured for interacting with the pressurization means such that by pressing the stiffening kinking-proof shell against the body part, the kinking-proof shell ensures appropriate stiffness of the blood pressure measuring system for pressure measurement. Such a stiffening kinking-proof shell allows for a straightforward design of the system. In particular, the stiffening kinking-proof shell may be pressed against the body part without interposition of any further stiffening element, i.e., between the stiffening kinking-proof shell, there is no further element which provides any stiffening function.

Preferably, structural resistance of the blood pressure measuring system, especially against compression forces, is provided by the kinking-proof shell, especially exclusively by the (stiffening) kinking-proof shell. The stiffening kinking-proof shell may be the sole component of the system which exhibits structural resistance against compression forces. As there is no need for applying any vacuum, pressure measurement may be more practicable and more reliable.

Preferably, the kinking-proof shell is a two-functions component which is configured to provide both buckling strength and deformation resistance, especially with respect to compression forces. In other words: The (stiffening) kinking-proof shell exhibits a deformation resistance or dimensional stability which ensures sufficient stiffness of the system, especially in conjunction with a pressure applied to the pressurization means. The (stiffening) kinking-proof shell may be the sole system component which is dimensionally stable, especially with respect to compression forces.

Preferably, the kinking-proof shell exhibits a surface, especially an inner lateral surface, which is configured for interaction with a pressure transducer, and which provides a seating for the pressure transducer and/or a pressure sensor pad (or cushion). A pressure sensor pad may contain a pressure transmitting hydraulic substance, e.g. a water-based gel, silicone oil or anything similar. The pressure sensor pad may comprise an inner pressure transducer or may be connected to an inner pressure transducer. Alternatively, the pressure sensor pad may be connected to an outer pressure transducer using appropriate pressure tubing filled with a pressure transmitting substance. Direct interaction between the kinking-proof shell and the pressure transducer or pressure-sensor pad may enhance accuracy of pressure measurements. The pressure transducer or pressure sensor pad may be fixed at the kinking-proof shell or—in case of use of an outer pressure transducer—on the outside of the actuator thus easily providing zeroing to heart-level by positioning the pressure transducer connected to the sensor pad to heart-level. Thereby, a dimensionally stable seating for the pressure transducer or pressure sensor pad may be provided by the kinking-proof shell itself. Thus, the kinking-proof shell may even fulfill three functions: providing a kinking-proof structure, providing stiffness, and providing a dimensionally stable seating for the pressure transducer or pressure sensor pad. Such a design is exceptionally practicable, especially with respect to disposables.

Preferably, the kinking-proof shell is a stiffening one-piece shell. Such a design allows for providing sufficient stiffness in a straightforward manner. The system may be simple and cost effective. In particular, handling of the system may be easy.

Preferably, the kinking-proof shell exhibits a free end having an angled front side. Such a shape may effectively prevent any blocking or interlocking of the free ends of the kinking-proof shell with each other. The front side may exhibit one adjacent surface portion. Alternatively, the front side may exhibit one or two adjacent surface portions which are arranged at an angle in the range of 40° to 135° with respect to each other, preferably in the range of 60° to 120°, more preferably 70° to 110°. The two adjacent surface portions may be arranged at a different angle with respect to a respective adjacent lateral surface of the kinking-proof shell, an inner surface portion preferably being less angled with respect to the inner lateral surface of the kinking-proof shell than the outer surface portion with respect to the outer lateral surface. An angle between the outer surface portion and the outer lateral surface may be in the range of e.g. 40° to 70°, and an angle between the outer surface portion and the outer lateral surface may be in the range of e.g. 20° and 55°. A smaller angle between the inner surface portion and the inner lateral surface may ensure that the inner surface portion exhibits a larger surface area than the outer surface portion. Such a design may effectively prevent any blocking or interlocking of the free ends.

Preferably, the kinking-proof shell exhibits a free end having a tapering, preferably a continuously decreasing thickness. In particular, the decreasing thickness may be provided with respect to overlapping portions. A tapering may provide a relatively flexible free end, which allows for overlapping of the free ends more easily. Also, at an overlapping portion, due to the overlap, an appropriate (sufficiently high) stiffness of the kinking-proof shell is ensured. In other words: Any tapering at the free end or at the overlapping portion does not negatively affect stiffness.

Preferably, the kinking-proof shell is dimensioned so as to overlap when surrounding the body part. In other words, the kinking-proof shell preferably completely surrounds the patient's body part, at least from the time when pressure is applied by the pressurization means. Thus, kinks or wrinkles can be avoided—or at least significantly reduced—along the whole circumference of the blood pressure measuring system. For example, the patient's body part may correspond to a patient's upper arm, leg or to a patient's wrist.

As kinks or wrinkles are avoided—or at least significantly reduced—due to the accommodation of the kinking-proof shell according to the present invention, overlapping portions of the blood pressure measuring system should be able to move or slide relatively to each other when its inner diameter is reduced due to the supply of pressurized fluid, preferably air, to the fluid bag of the actuator. Therefore, the blood pressure measuring system, especially the kinking-proof shell, is preferably designed so that overlapping portions can easily slide relatively to each other. For example, surface portions of the blood pressure measuring system that are in direct sliding contact with each other may exhibit a relatively low friction coefficient, e.g. by choosing the materials and/or the surface structures correspondingly. The term "low friction coefficient" in the context of the present invention refers to a friction coefficient (of two flat surfaces) of less than 0.5, preferably of less than 0.3, more preferably of less than 0.2, and even more preferably of less than 0.1. Sliding may also be enhanced by providing the blood pressure measuring system with a substantially cylindrical or, preferably, conical shape.

Preferably, the blood pressure measuring system exhibits a textile or textile-like layer which is arranged so as to be located between the kinking-proof shell and the body part. The textile layer may provide a favorable friction coefficient between the body part and the kinking-proof shell. Also, the textile layer may ensure that any relative motion of the kinking-proof shell with respect to the body part does not evoke squeezing or pinching of the body part. Preferably, the textile layer is provided at least on an inner side, especially an inner lateral surface, of the kinking-proof shell. Such an arrangement may ensure that any direct contact between the kinking-proof shell and the body part is prevented.

Preferably, the textile layer is made of a multifilament, wherein the material of the textile layer preferably is polyamide. Such a textile layer may be provided with high resistance or resilience. Also, such a textile layer can be provided with a small thickness. The multifilament textile layer may be provided by an arrased or machine-knit textile which exhibits good elasticity.

Preferably, the textile layer is a socklike layer (a kind of lining) provided on an inner lateral surface of the kinking-proof shell. A socklike layer or lining may ensure that any friction between the kinking-proof shell and the body part is minimum. Alternatively or in addition, the textile layer may be provided by a flock coating, at least in sections.

According to one specific embodiment, the textile layer is a hose or stocking which bounds or covers the kinking-proof shell, especially both lateral surfaces of the kinking-proof shell. In particular, the textile layer may prevent any adhesion of the kinking-proof shell on the body part.

Preferably, the textile layer exhibits a mass per meter in the range between 0.1 and 15 g/1000 m (tex), more preferable between 0.3 and 10 g/1000 m, further preferred between 1 and 5 g/1000 m, especially 2 g/1000 m. It has been found that such a fine or thin layer may ensure favourable sliding properties.

Preferably, the kinking-proof shell exhibits a slide coating or surface finishing which allows for a friction coefficient of less than 0.5, preferably of less than 0.3, more preferably of less than 0.2, and even more preferably of less than 0.1, at least in overlapping surface portions. The coating may be provided e.g. on an inner lateral surface and/or an outer lateral surface. The coating may be e.g. a polytetra-fluor-ethylene coating.

A slide coating or surface finishing is preferably provided in conjunction with a textile layer. The textile layer may ensure advantageous sliding properties of the kin king-proof shell with respect to the body part. A slide coating or surface coating may be provided especially at least in overlapping portions of the kinking-proof shell, in order to ensure advantageous sliding properties of the overlapping portions of the kinking-proof shell with respect to each other. For example, a textile layer may be provided on an inner lateral surface of the kinking-proof shell, especially for contact with the body part, and a slide coating may be provided on an outer lateral surface of the kinking-proof shell, at least in overlapping portions.

Alternatively or in addition to a slide coating or a surface finishing, kinking-proof shell may be provided with a porous material or made of a porous material, at least in sections, especially in overlapping portions. The porous material may be filled with any substance or particles reducing friction.

According to one specific embodiment, the textile layer is a hose or stocking which covers lateral surfaces of the kinking-proof shell which are arranged so as to be in contact with the body part and the pressurization means, and the slide coating or a surface finishing is provided at least in overlapping surface portions contacting each other. Such an arrangement may ensure both advantageous haptic properties and low frictional forces.

In the following, referring to a flexible element, one specific embodiment is described. Such a flexible element is not necessarily required. Rather, the present invention is also based on the finding that such a flexible element is not required in case the kinking-proof shell is configured for ensuring stiffness of the blood pressure measuring system on its own. Nonetheless, a stiffening kinking-proof shell may be provided in conjunction with a flexible element also.

The blood pressure measuring system may further comprise a flexible element configured to at least partially surround the body part and having a stiffening element configured to stiffen the flexible element. Such a flexible element is described in detail in DE 10 2009 39257 A1. The content of DE 10 2009 39257 A1 is incorporated herein by reference. Due to the stiffening element, the flexible element is changeable from a non-stiffened state to a stiffened state. For example, the flexible element with the stiffening element may be formed by an air-tight pouch that includes essentially incompressible elements having a volume in vacuum configured to change less than 50%, preferably less than 25%, more preferably less than 10%, and even more preferably less than 1% in comparison to a volume at atmospheric pressure. The essentially incompressible elements are, for instance, plastic granules, rice, particles made of polystyrene or a similar plastic, shredded paper, paper pellets, sheets of paper, Styrofoam beads, sawdust, salt, any powder or similar elements. The essentially incompressible elements located in the air-tight pouch are preferably a mixture of different types of incompressible elements. As the incompressible elements, special preference is given to sheets of paper or of another material that are layered to form a stack. After placing the blood pressure measuring system with the flexible element in a non-stiffened state around a patient's body part, pressure may be applied to the body part by the pressurization means, e.g. pressure may be applied to a fluid bag of an actuator. Then, air may be evacuated from the air-tight pouch of the flexible element, thereby stiffening the flexible element. The flexible element may be arranged (sandwiched) between the pressurization means and the patient's body part, especially between the kinking-proof shell and the patient's body part. The stiffened flexible element, thus, avoids (or at least significantly reduces) pressure oscillations stemming from the patient's heart beats to be attenuated by the pressurization means which may comprise e.g. a fluid bag. A pressure sensor unit—that may be located at least partially between the flexible element and the patient's body part—can therefore obtain signals of high measurement accuracy, when the flexible element is in its stiffened state during the measurement.

If the incompressible elements are essentially formed by sheets of paper or of another material that are layered to form a stack, each layer may comprise a plurality of sub-areas that are displaceable relatively to each other, wherein each subarea may be connected with at least one other subarea of the same layer. The subareas may be interconnected with each other by connection elements. Also, the connection elements may be integrally formed with the subareas. The connecting elements may be formed so as to function as hinges for the subareas interconnected by the connecting elements. That way, the flexible element is extremely flexible in its non-stiffened state and, thus, can easily adapt to the three-dimensional shape of the patient's body part. However, in its stiffened state, when a vacuum is applied to the air-tight pouch, the stacked layers are pressed against each other, thereby forming a very stiff force-fitted compound.

If the blood pressure measuring system comprises a flexible element having the stiffening element, the kinking-proof shell may be sandwiched between the pressurization means, e.g. a pressure actuator with the fluid bag, on the one hand and the flexible element having the stiffening element on the other hand. At their edge regions, the pressurization means and the flexible element having the stiffening element may be connected to each other, thereby securely enclosing the kinking-proof shell. For example, the pressurization means may be irreversibly connected to the flexible element having the stiffening element, e.g. by heat welding or by adhesive bonding.

Furthermore, if the blood pressure measuring system comprises a flexible element having the stiffening element, the kinking-proof shell may be attached to an outer surface of the flexible element having the stiffening element. For example, the kinking-proof shell may be irreversibly attached to the flexible element having the stiffening element, e.g. by heat welding or by adhesive bonding. However, in a specific embodiment, the flexible element having the stiffening element comprises on its outer surface at least one sleeve, e.g. made from a plastic material, which at least one sleeve is adapted for housing the kinking-proof shell. The kinking-proof shell may be housed in the at least one sleeve in such a way that it can move, e.g. slide, relatively to the flexible element having the stiffening element. With such a configuration, the flexible element having the stiffening element and the kinking-proof shell may better adapt to the shape of the patient's body part when pressure is applied by the pressurization means.

Furthermore, if the blood pressure measuring system comprises a textile layer and further comprises a flexible element having the stiffening element, the textile layer may be provided on a surface of the flexible element and/or a surface, especially an outer surface, of the kinking-proof shell.

Preferably, the kinking-proof shell is made from metal and/or plastic, in particular fiber-reinforced plastic. For example, the kinking-proof shell might be made from or coated with a thermoplastic material, preferably made from polyurethane or a polyolefin, more preferably made from polyethylene and/or polytetrafluorethylene (PTFE) or coated with polytetrafluorethylene. For example, the kinking-proof shell might be made from a thermoplastic material which provides a surface on which adhesives may adhere durably. If the kinking-proof shell comprises fiber-reinforced plastic material, the fibers may be natural fibers, organic fibers or inorganic fibers. The material and the shape, in particular the thickness, of the kinking-proof shell should be chosen so that the kinking-proof shell, on the one hand, is stiff enough not to buckle when pressure is applied by the pressurization means (especially in case no additional flexible element is provided), and that the kinking-proof shell, on the other hand, is flexible enough so as to allow a reduction of its inner diameter when pressure is applied by the pressurization means. In particular, if the kinking-proof shell is substantially made from plastic material, experimental tests performed by the inventors have shown that the kinking-proof shell preferably exhibits a thickness of between about 0.25 mm and about 6 mm, more preferably between about 1 mm and about 3 mm, even more preferably between about 1.0 mm and about 2.0 mm. For example the kinking-proof shell may have a thickness of about 1.5 mm, especially for adults. Or the kinking-proof shell may have a thickness of about 0.5 mm, especially for infants and babies. For example the kinking-proof shell may be made from polyethylene (PE), having a thickness of about 1.5 mm. It has been found that such a thickness may ensure sufficient stiffness, even in case no additional flexible element is provided.

The thickness of the kinking-proof shell may be reduced, preferably gradually, at the edge regions of the kinking-proof shell. Thus, the kinking-proof shell may have some kind of ramp-shaped form at its edge regions so as to promote relative sliding of the overlapping portions of the blood pressure measuring system.

At the edge regions, the kinking-proof shell may exhibit roundings and/or chamfers and/or taperings. Such a shape may facilitate sliding of one free end of the kinking-proof shell with respect to the other (overlapping) free end.

Experimental tests of the inventors have also shown that it is advantageous—in order to avoid kinks on the one hand and to allow a reduction of the inner diameter on the other hand—that the kinking-proof shell preferably exhibits a modulus of elasticity of more than 50 MPa, more preferably of between about 100 MPa and about 10 GPa, even more preferably of between about 200 MPa and about 1 GPa.

The kinking-proof shell may exhibit a substantially cylindrical configuration, so that the blood pressure measuring system can be easily applied to the patient's body part, preferably the patient's upper arm, without having to wrap the system around that body part. Preferably, the kinking-proof shell, however, exhibits a rather conical configuration so as to better adapt to the shape of the body part. A conical configuration may be provided by a spiral-shaped arrangement of the kinking-proof shell. In other words: The kinking-proof shell is arranged for twisting when overlapping portions slide with respect to each other.

To have close contact with the patient's body part during blood pressure measurement is important for the blood pressure measuring system in order to obtain results of high quality. However, as the patient's body part, e.g. the patient's upper arm, may have a complex shape (i.e. not an ideal cylindrical or conical shape, but a rather concave and/or convex shape), according to one specific embodiment, the kinking-proof shell may comprise a plurality of individual shell elements or shell sections. In case the kinking-proof shell is a one-piece shell, the kinking-proof shell may exhibit shell sections. For example, especially in case the blood pressure measuring system does not comprise any additional flexible element, the plurality of individual shell sections may be interconnected such that the stiffness of the kinking-proof shell is not reduced, or such that the stiffness only varies continuously, but not discontinuously (discretely) in stages nor at any different definite levels. In other words: The plurality of individual shell sections may also be provided by different portions or sections of a one-piece shell. The different portions or sections may exhibit, e.g., differing thicknesses and/or differing moduli of elasticity. Alternatively, especially in case the blood pressure measuring system comprises an additional flexible element, the kinking-proof shell may comprise a plurality of strap-like shell sections or shell elements (substantially arranged in parallel and preferably spaced apart from each other), each section or element being adapted for surrounding the patient's body part.

In case the blood pressure measuring system comprises an additional (optional) flexible element with a stiffening element, as described above, portions of the flexible element located substantially between two adjacent shell sections or shell elements may function as hinges (as long as the flexible element is not stiffened), thereby allowing the kinking-proof shell to well adapt to the shape of the patient's body part. When the flexible element is then stiffened by the stiffening element, also the hinge-portions are stiffened, thereby impeding relative movement of the individual shell sections or shell elements.

If the kinking-proof shell comprises a plurality of individual shell elements or shell sections, preferably at least two elements or sections of the plurality of individual shell elements or shell sections are arranged substantially parallel to each other, each extending in a circumferential direction of the body part when the blood pressure measuring system surrounds the body part. Such a configuration provides good flexibility of the system in a direction perpendicular to the circumferential direction of the patient's body part. Thus, the shape of the kinking-proof shell may adapt to the shape of the patient's body part (e.g. a concave and/or convex shape) more effectively. At the same time, sufficient stiffness can be ensured.

Additionally or alternatively, at least two elements or sections of the plurality of individual shell elements or shell sections may be arranged adjacent to each other in a circumferential direction of the body part when the blood pressure measuring system surrounds the body part. Such a configuration provides good flexibility of the system in the circumferential direction of the patient's body part. The at least two adjacent shell elements may be connected to each other by at least one flexible link, especially in case the blood pressure measuring system comprises an additional flexible element. The at least one flexible link preferably restricts the maximal bending angle range between the adjacent shell elements. For example, the maximal bending angle range may be limited to 90°, preferably to 45° or even less. Furthermore, at least one link—preferably all links—may comprise a backing member which allows for angles between two adjacent shell elements smaller than a predetermined maximal angle (e.g. 180°) while at the same time inhibiting any bending angles greater than the predetermined maximal angle. This way, a shape different from circular, e.g. an elliptic shape, may be enabled and mechanical stress in the shell material is reduced, while kinking is still inhibited. In addition, the body part is not forced to take on a circular cross-section.

Preferably, at least two sections of the plurality of individual shell sections are separated from each other by a groove, the groove preferably being wedge-shaped. A groove, incision or indentation may facilitate twisting of the kinking-proof shell, especially in case it is wedge-shaped. A groove, incision or indentation may define a bending direction of the kinking-proof shell. Preferably, the groove extends in a direction which is orthogonal to a circumferential direction of the kinking-proof shell when the blood pressure measuring system surrounds the body part. The plurality of individual shell sections may be separated from each other by a plurality of grooves which are arranged substantially parallel to each other. Such an arrangement may ensure that specific stiffness properties are maintained, especially with respect to specific directions. Preferably, the groove, incision or indentation exhibits a depth which is lower than factor ⅓, preferably factor ¼, further preferred factor ⅕, of the wall thickness of the kinking-proof shell. Such a relatively low depth allows for high stiffness as well as for a spiral-shaped arrangement of the kinking-proof shell.

The blood pressure measuring system may further comprise a pressure sensor unit, wherein the pressure sensor unit is preferably arranged so as to be at least partially located between the kinking-proof shell and the body part, preferably next to the body part, when the blood pressure measuring system surrounds the body part. The pressure sensor unit may comprise a relatively small gel or oil cushion or the like provided in direct contact with the patient's body part. The pressure sensor unit preferably further comprises a pressure transducer. The pressure transducer may be located in or on the gel cushion. Alternatively, the pressure transducer may be located remote from the measuring site at the patient's body part (i.e. remote from the gel cushion), wherein the pressure transducer may be connected to the gel cushion e.g. via a tubing or hose filled with an appropriate gel or other fluid.

Arranging the pressure sensor unit that way—instead of measuring the pressure in the fluid bag of the pressurization means, as usually done in known devices—is advantageous, because the measured pressure signal is significantly less affected by attenuation phenomena caused by the fluid bag. Thus, the measurement accuracy can be further increased.

Preferably, the pressure sensor unit comprises a pressure transducer or pressure sensor pad which is arranged at an inner side or on an inner lateral surface of the kinking-proof shell. Such an arrangement allows for high measurement accuracy. In particular, the pressure transducer or pressure sensor pad may be arranged between an inner lateral surface of the kinking-proof shell and a/the textile layer covering the inner lateral surface. The pressure transducer or pressure sensor pad may be fixed on the inner lateral surface. Alternatively, the pressure transducer may be integrated in the kinking-proof shell, at least partially.

Preferably, the pressure transducer or pressure sensor pad extends in a circumferential direction of the kinking-proof shell when the blood pressure measuring system surrounds the body part. Such an arrangement facilitates handling of the system. Correct or appropriate positioning of the system with respect to the body part may be facilitated. In particular, the pressure transducer may extend along a section of at least factor ⅕ or ¼ of the absolute measurement of the kinking-proof shell in the circumferential direction. Such an extension or elongated arrangement of the pressure transducer or pressure sensor pad allows for fast and easy pressure measurements, reducing any risk of erroneous evaluation of the pressure. The pressure transducer or pressure sensor pad may even extend along all sections which do not overlap. Such a relatively elongated configuration allows for facilitating pressure measurement, especially as any tissue pressure wave resulting from an arterial pressure wave may be captured more reliably.

Preferably at least the pressurization means and the kinking-proof shell, more preferably all components of the system, are connected to each other in such a way as to form a single unit. Such a configuration allows the system to be wrapped as a single unit around the patient's body part for measuring the patient's blood pressure, which in turn allows for easy and fast application of the system and minimizes the risk of faulty operation thereof.

The above mentioned object is also achieved by the features of the independent method claim. In particular, the object is achieved by a method of applying a blood pressure measuring system configured to surround a patient's body part, especially a blood pressure measuring system according to any of the inventive embodiments as described above, comprising the steps:

providing a kinking-proof shell around the body part between pressurization means and the body part, applying pressure to the pressurization means, and pressing the kinking-proof shell against the body part. Such a method provides the advantages as discussed above in context with the inventive blood pressure measuring system. Preferably, the blood pressure measuring system is stiffened by pressing the kinking-proof shell against the body part. Such a method may be carried out fast. Evacuation is not required. Handling is easy. Also, pressure measurement can be carried out directly on a surface of the kinking-proof shell.

The method may be carried out in conjunction with the embodiments of the system as described above, especially in conjunction with the embodiments of the kinking-proof shell as described above. In particular, stiffening the blood measurement system may be carried out in conjunction with a textile layer.

In the following, the present invention is illustrated with reference to an exemplary embodiment shown in the accompanying drawings, in which:

FIG. 1a shows an embodiment of a blood pressure measuring system in a deflated state, wherein the blood pressure measuring system does not comprise a kin king-proof shell, and therefore does not form part of the present invention;

FIG. 1b shows the embodiment of FIG. 1 a in an inflated state;

FIG. 2a shows an embodiment of a blood pressure measuring system according to the present invention in a deflated state;

FIG. 2b shows the inventive embodiment of FIG. 2a in an inflated state;

Figures 7A, 7B:
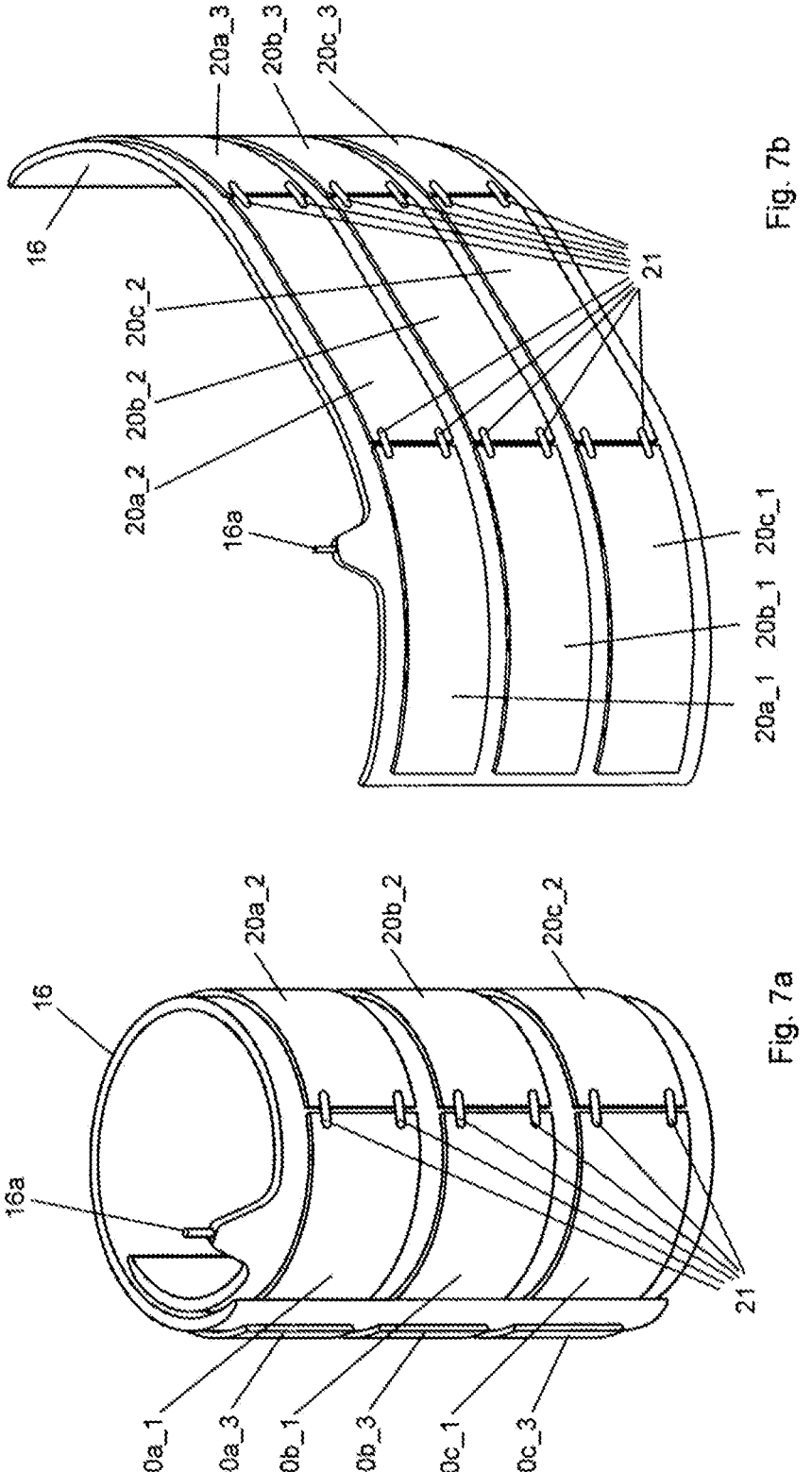
FIG. 7a shows a three-dimensional view (similar to the view shown in FIG. 4a) of a second inventive embodiment without the pressure actuator for the sake of clarity.
Figure 8B:
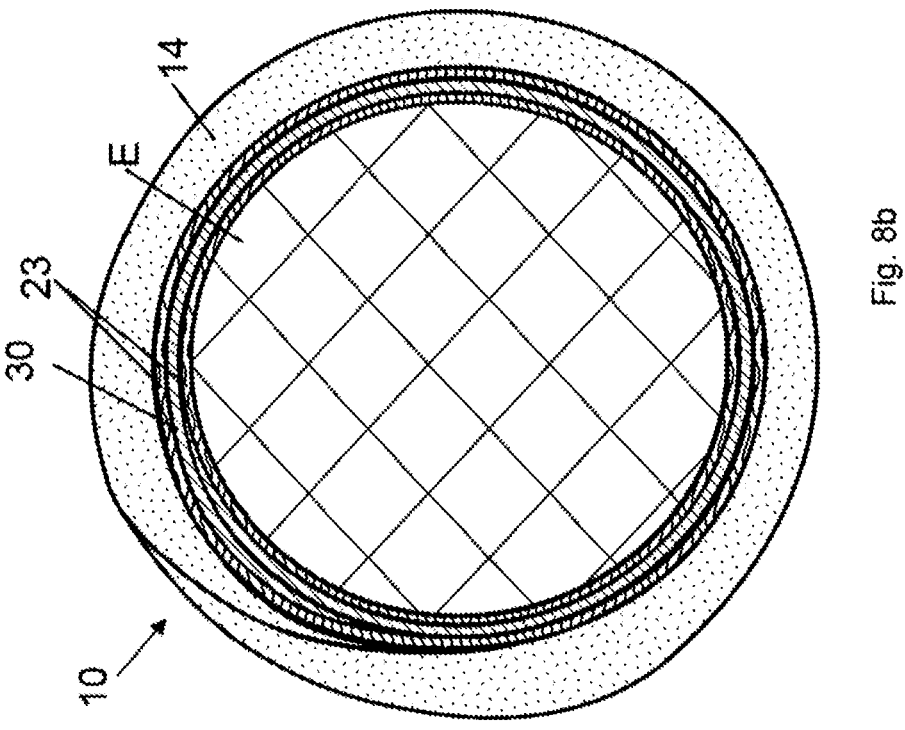
Figure 8A:
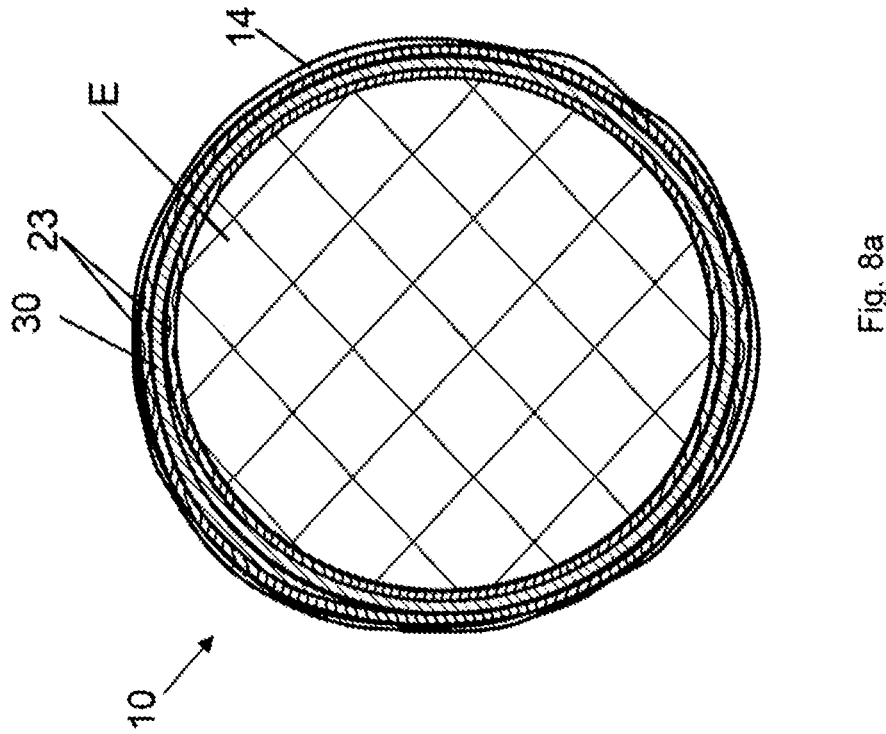
Figure 8C:
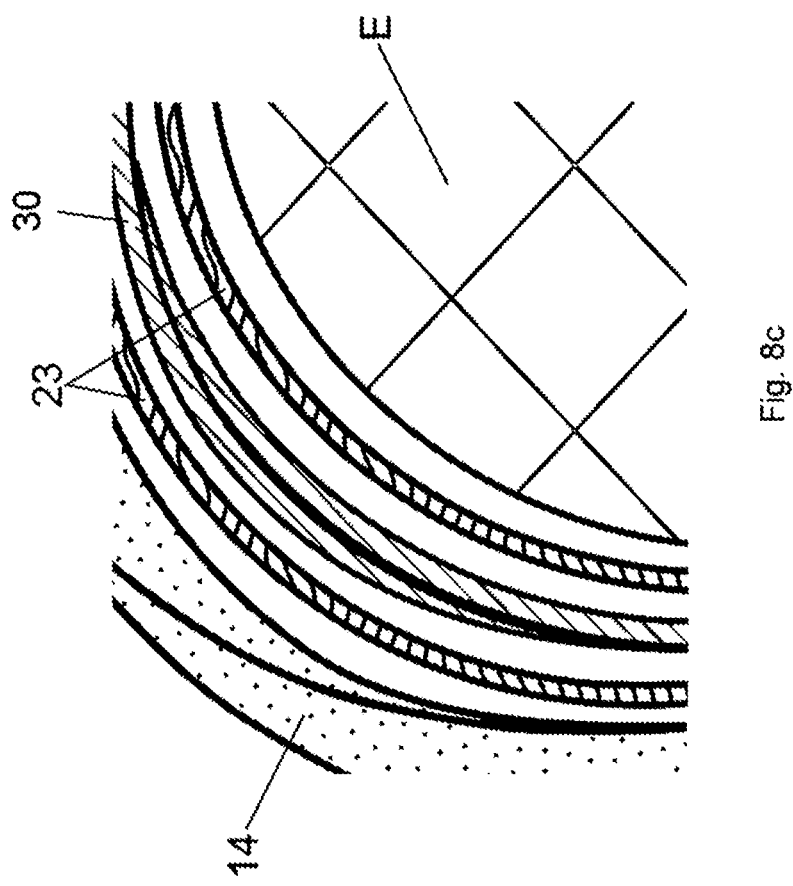
Figure 9:
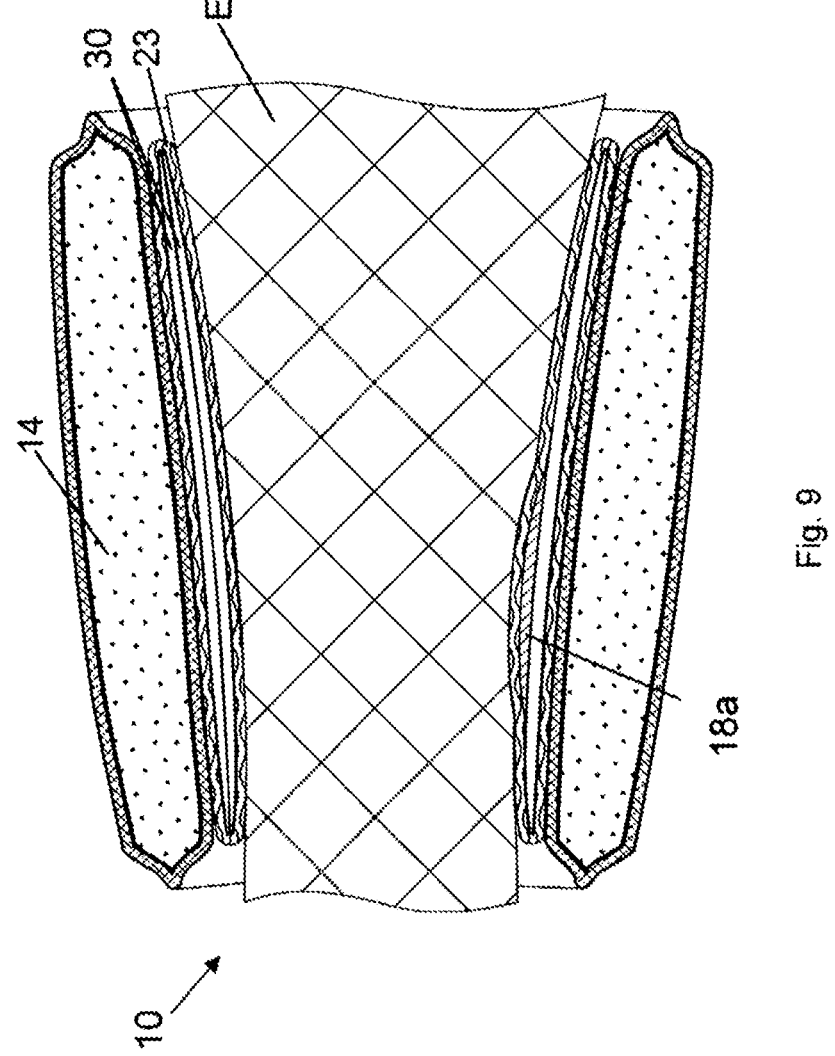
Figure 10:
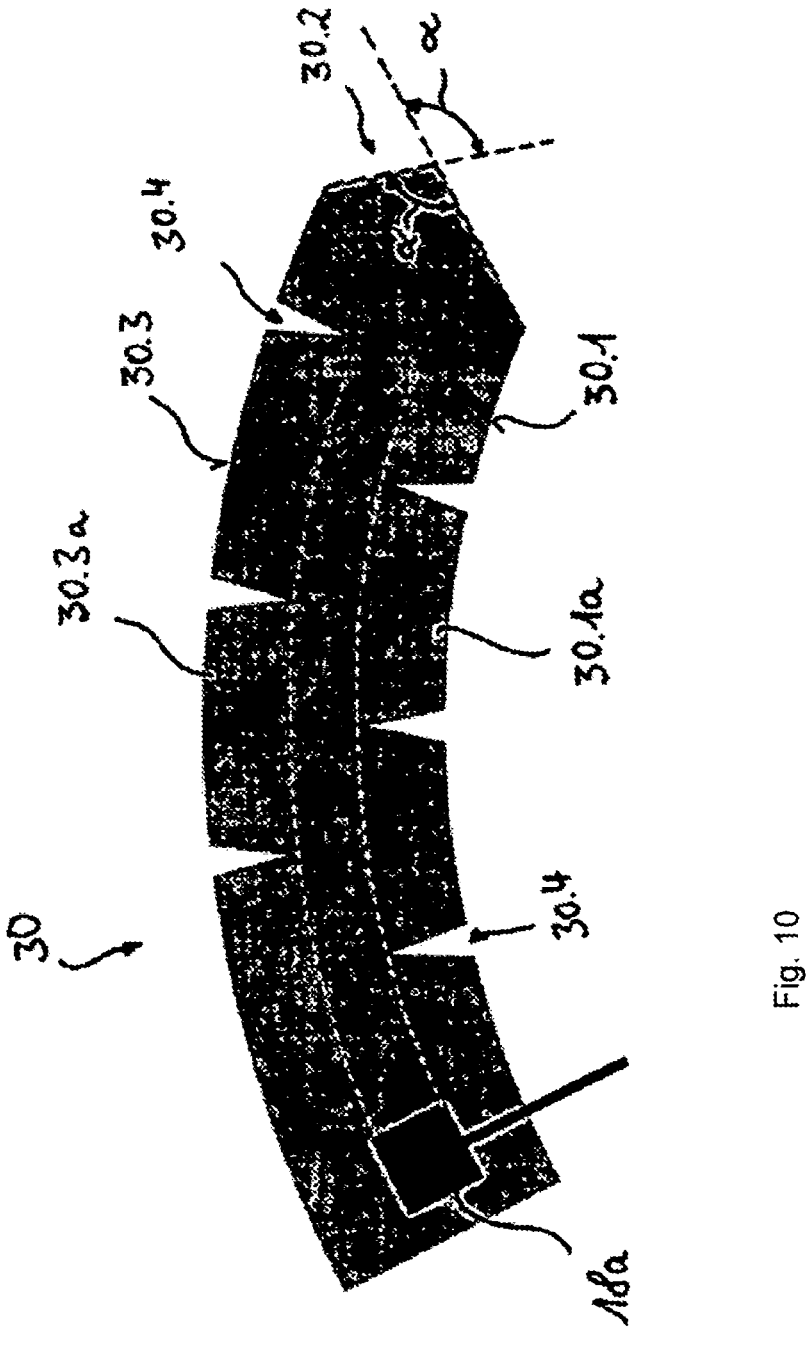

FIG. 7*b* shows a three-dimensional view of the second embodiment of FIG. 7*a* in a substantially flat configuration;

FIG. 8*a* shows a section view of a blood pressure measuring system according to one preferred embodiment of the present invention in a deflated state;

FIG. 8*b* shows a section view of the inventive embodiment of FIG. 8*a* in an inflated state;

FIG. 8*c* shows a detailed view of a segment of the inventive embodiment of FIG. 8*b*;

FIG. 9 shows a cross-sectional view of the inventive embodiment of FIG. 8*b*; and FIG. 10 shows a cross-sectional view of a stiffening kinking-proof shell which may be provided as a component of any of the inventive embodiments.

FIGS. 1*a* and 1*b* show an embodiment of a blood pressure measuring system 10' which embodiment does not comprise a kinking-proof shell and therefore does not form part of the present invention. This embodiment is described only to illustrate the disadvantages of blood pressure measuring systems known in the art. The shown blood pressure measuring system 10' comprises a pressurization means which in turn comprises a pressure cuff 12' having a fluid bag 14', the pressure cuff 12' surrounding a patient's body part E, for example a patient's upper arm. Furthermore, the shown blood pressure measuring system 10' also comprises a flexible element 16' having a stiffening element. The flexible element 16' also surrounds the body part E and is sandwiched between the body part E and the pressurization means comprising the pressure cuff 12' with the fluid bag 14'.

To measure the blood pressure of a patient, the blood pressure measuring system 10' is applied to the patient's body part E with the fluid bag 14' of the pressure cuff 12' being in a deflated state, as shown in FIG. 1*a*. Then, a pressurized fluid, preferably air, is applied to the fluid bag 14', thereby inflating the fluid bag 14', as illustrated in FIG. 1*b*. Afterwards, the flexible element 16' may be stiffened by the stiffening element so as to reduce attenuation effects of the inflated fluid bag 14' during measurement. A pressure sensor unit (not shown in FIGS. 1*a* and 1*b*) is preferably provided at least partially between the flexible element 16' and the patient's body part E. The flexible element 16' with the stiffening element is preferably formed by an airtight pouch that includes essentially incompressible elements, preferably sheets of paper that are layered to form a stack. Preferably each sheet of paper has a cutting pattern so as to provide high flexibility to the flexible element 16' in its non-stiffened state. For stiffening the flexible element 16', a vacuum may be applied to the air-tight pouch, so that the stacked paper layers are pressed against each other, thereby forming a stiff force-fitted compound.

As illustrated in FIG. 1*b*, the problem of this blood pressure measuring system 10' is that wrinkles or kinks are formed at a compression acting surface (i.e. the interior surface) of the fluid bag 14' when pressure is applied to the fluid bag 14'. These wrinkles or kinks cause also the flexible element 16' to buckle. Thus, part of the skin of the body part E can be trapped in the valley portions of the kinks of the flexible element 16', which may cause slight subcutaneous bleeding at the measuring site. Moreover, the cavities resulting from the wrinkles and kinks in the compression acting surface of the fluid bag 14' and/or in the flexible element 16' reduce the achievable measurement accuracy.

The wrinkles or kinks shown in FIG. 1*b* are formed substantially because the overlapping portions of the flexible element 16' do not (sufficiently) slide with respect to each other when pressure is applied to the fluid bag 14'. One reason for this is that the flexible element 16' in its non-stiffened state is not kinking-proof. Another reason is that the overlapping portions of the flexible element 16' exhibit poor sliding properties, e.g. due to geometric reasons.

To overcome this problem, the blood pressure measuring system 10 according to the present invention additionally comprises a kinking-proof shell 20 that is arranged between the pressurization means, comprising pressure actuator 12 with the fluid bag 14, and the body part E, as illustrated in FIGS. 2*a* and 2*b*. More specifically, in the particular embodiment disclosed in FIGS. 2*a* and 2*b*, the kinking-proof shell 20 is arranged (sandwiched) between the pressure actuator 12 with the fluid bag 14 and the flexible element 16. The pressure actuator 12 with the fluid bag 14 and the flexible element 16 can be attached, e.g. by heat welding or by adhesive bonding, to each other at their edge regions so as to securely accommodate the kinking-proof shell 20 in between.

In this embodiment, the kinking-proof shell 20 is preferably made from plastic material, such as polyethylene. The thickness of the kinking-proof shell 20 is chosen so that the kinking-proof shell 20 does not buckle when pressure is applied to the fluid bag 14, while at the same time the kinking-proof shell 20 is flexible enough to allow for a certain deformation of the kinking-proof shell 20. That is, when pressure is applied to the fluid bag 14, overlapping edge regions of the kinking-proof shell 20 move or slide relatively to each other so as to reduce the diameter of the kinking-proof shell 20. However, the kinking-proof shell 20 thereby remains substantially ring-shaped.

Due to the provision of the kinking-proof shell 20 according to the present invention, the formation of wrinkles or kinks in the compression acting surface of the fluid bag 14' can be significantly reduced and the formation of wrinkles or kinks in the flexible element 16 can be even completely avoided, as shown in FIG. 2*b*. Therefore, no subcutaneous bleeding at the measuring site occurs and the measurement accuracy is significantly improved.

Figure 3:
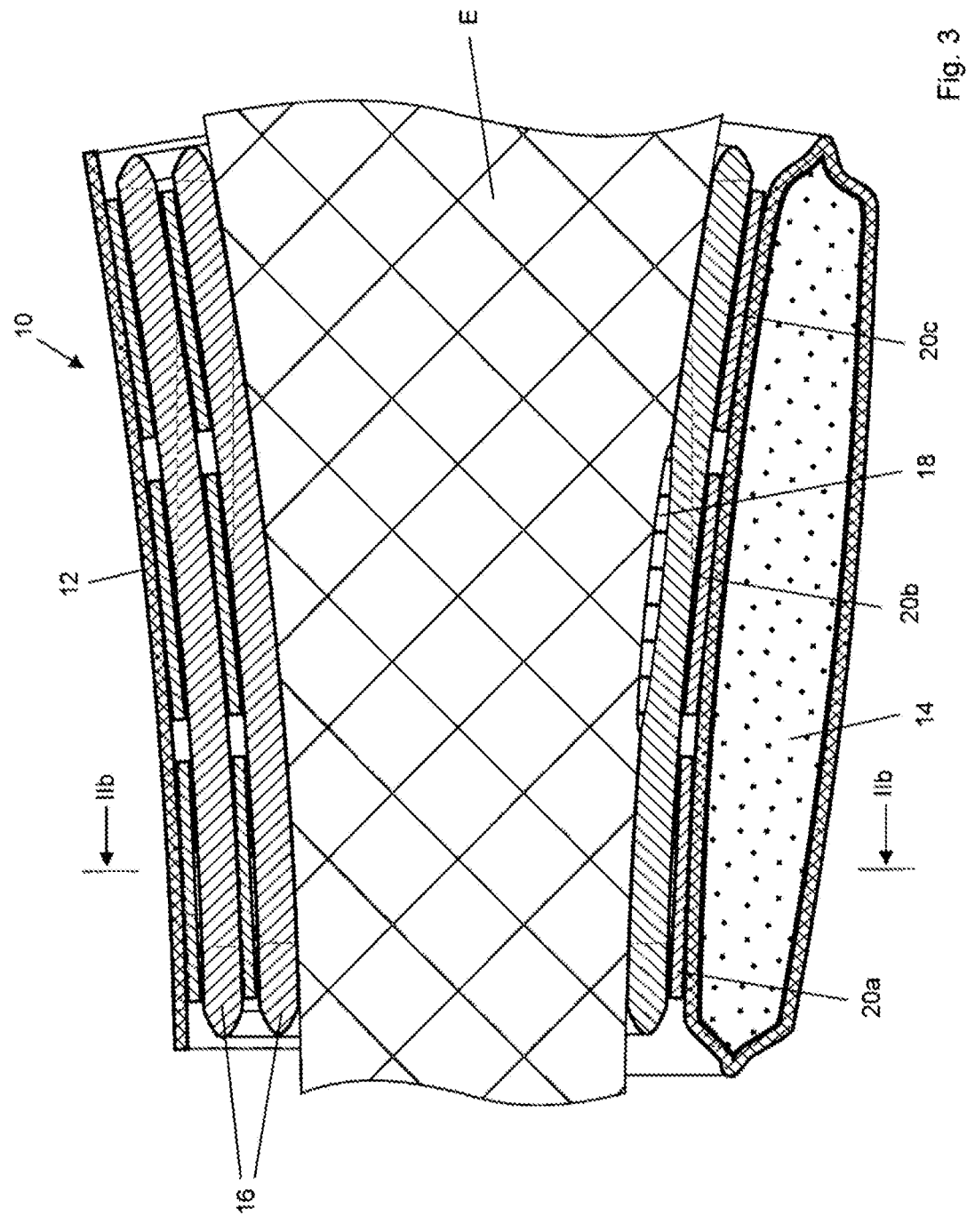
FIG. 3 shows a cross-sectional view of the inventive embodiment taken along line of FIG. 2b.

A cross-sectional view of the blood pressure measuring system 10 according to line of FIG. 2*b* is shown in FIG. 3. As can be seen in FIG. 3, the kinking-proof shell 20 comprises three individually formed shell elements 20*a*, 20*b* and 20*c*, being arranged substantially in parallel to each other. The shell elements 20*a*, 20*b* and 20*c* exhibit a substantially strap-shaped form surrounding the patient's body part E. Forming the kinking-proof shell 20 from a plurality of individual elements 20*a*, 20*b* and 20*c* has the advantage that the kinking-proof shell better fits or adapts to the shape of the body part E. Preferably, the individual shell elements 20*a*, 20*b* and 20*c* are slightly spaced from each other so as to provide a high degree of flexibility. Preferably, the individual shell elements 20*a*, 20*b* and 20*c* are attached to the outer surface of the flexible element 16. More preferably, the individual shell elements 20*a*, 20*b* and 20*c* are held in pockets or sleeves formed on the outer surface of the flexible element 16, the pockets or sleeves preferably being made from plastic material. That way, the regions of the flexible element 16 located substantially between the individual shell elements 20*a*, 20*b* and 20*c* can act as hinge portions for the shell elements 20*a*, 20*b* and 20*c*, at least as long as the flexible element 16 is not stiffened by the stiffening element. When the flexible element 16 is stiffened, also the hinge portions are stiffened, thereby inhibiting any (angular) movement of the shell elements 20*a*, 20*b* and 20*c* relative to each other.

In FIG. 3, also a (relatively small) gel cushion 18 is shown which forms part of a pressure sensor unit. The pressure sensor unit further comprises a pressure transducer (not shown) which is operatively connected, preferably via a fluid filled tubing, with the gel cushion 18. The gel cushion 18 is arranged between the kinking-proof shell 20 and the body part E, and more particularly, in the shown embodiment, between the flexible element 16 and the body part E. That way, both, the flexible element 16, when it is stiffened, and the kinking-proof shell 20 minimize adverse attenuation effects of the fluid bag 14 on the pressure sensor unit, thereby further improving the measurement accuracy.

Notably, line IIb-IIb in FIG. 3 indicates the cross-sectional view shown in FIG. 2b.

Figure 4B:
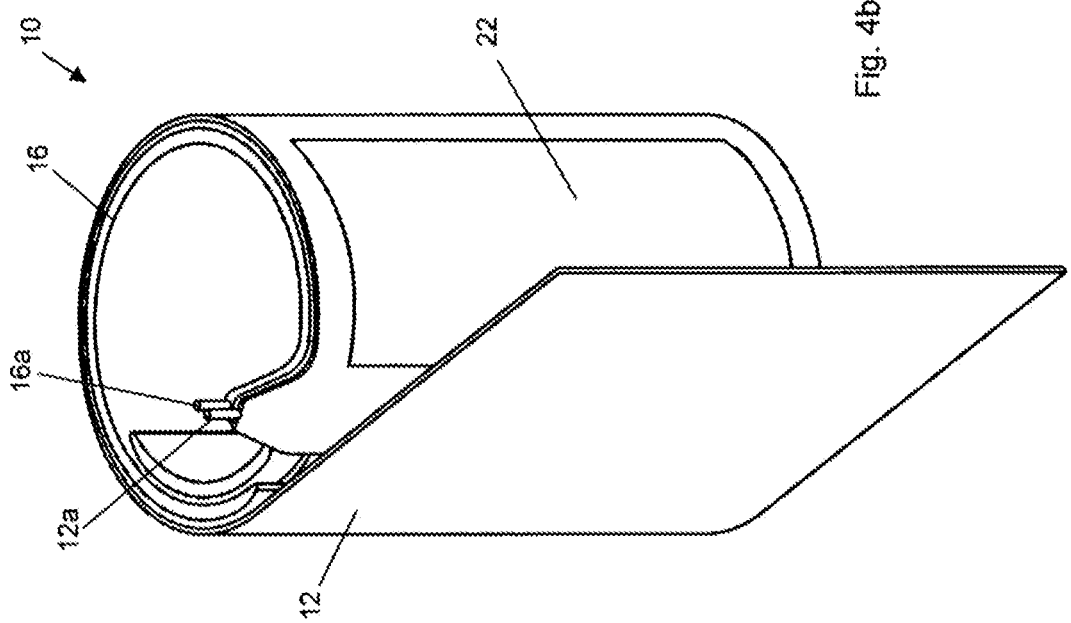
FIG. 4b shows a view similar to the one of FIG. 4a but with the pressure actuator (comprising the fluid bag)
Figure 4A:
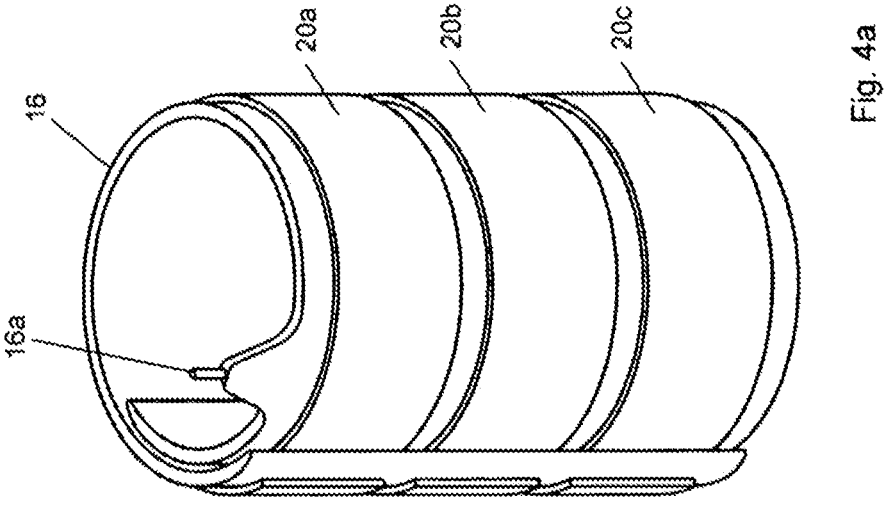
FIG. 4a shows a three-dimensional view of the inventive embodiment but without the pressure actuator (comprising the fluid bag) for the sake of clarity.

FIGS. 4a and 4b show three-dimensional views of the blood pressure measuring system 10 according to the present invention, wherein—only for the sake of clarity—the pressurization means comprising the pressure actuator 12 with the fluid bag 14 is not illustrated in FIG. 4a. As can be seen from FIGS. 4a and 4b, the flexible element 16 comprises an evacuation port 1 6a through which the air-tight pouch of the flexible element 16 can be evacuated thereby stiffening the flexible element 16. Similarly, the pressure actuator 12 comprises a pressure port 12a to apply pressurized fluid (preferably air) to the fluid bag 14 of the pressure actuator 12. Moreover the pressure actuator 12 comprises fastening means 22, such as hook-and-loop fastener, for attaching (preferably reversibly) the two longitudinally ends of the pressure actuator 12 to each other, which ends usually overlap when performing the blood pressure measurement.

Notably, all the above described components of the inventive blood pressure measuring system are preferably connected to each other in such a way as to form a single unit which can be wrapped around the patient's body part for measuring the patient's blood pressure. Such a configuration of the inventive blood pressure measuring system 10 allows for easy and fast application and minimizes the risk of faulty operation thereof.

Figure 5:
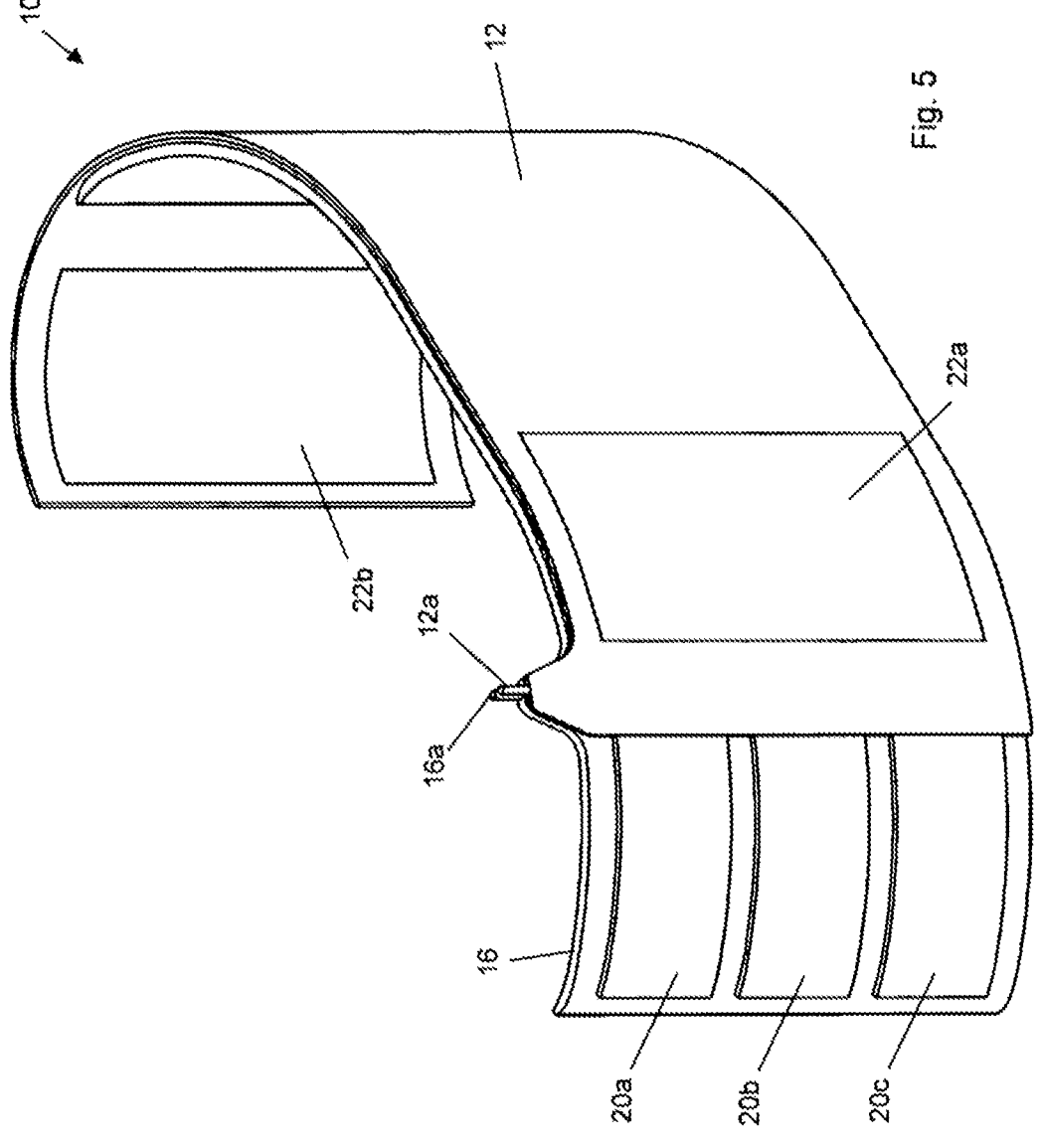
FIG. 5 shows a three-dimensional view of the inventive embodiment in a substantially flat configuration.

FIG. 5 shows a three-dimensional view of the blood pressure measuring system 10 according to the present invention, wherein the blood pressure measuring system 10 is shown in a substantially flat, i.e. substantially non-wrapped, configuration. As can be seen from FIG. 5, the pressure actuator 12 comprises two complementary formed fastening means 22a and 22b, such as hook-and-loop fastener. It should be noted that both ends of the pressure actuator 12 of the blood pressure measuring system 10 according to the present invention may alternatively also be irreversibly be attached to each other. If both ends of the pressure actuator 12 are irreversibly attached to each other, it is not necessary to wrap the pressure actuator 12 around the patient's body part E, thus, making the processes of applying the blood pressure measuring system easier.

Figure 6:
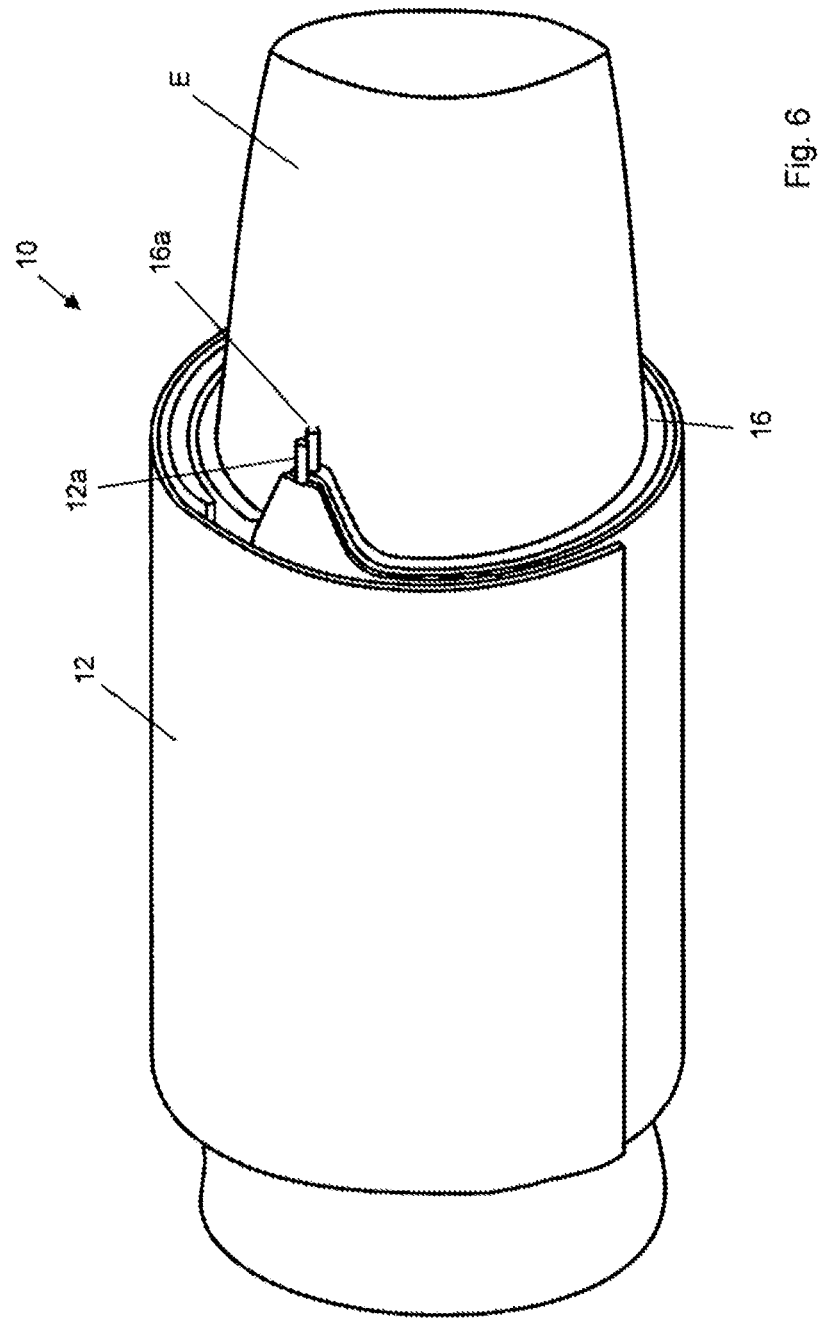
FIG. 6 shows a three-dimensional view of the inventive embodiment wrapped around a patient's body part.

FIG. 6 shows a three-dimensional view of the blood pressure measuring system 10 according to the present invention, when applied to the patient's body part E, preferably to a patient's upper arm.

It should be generally noted that providing the flexible element 16 with the stiffening element to the blood pressure measuring system 10 is beneficial but not essential for the present invention. The known blood pressure measuring systems may equally be improved according to the present invention if no flexible element 16 (that can be stiffened) is provided.

Finally, FIGS. 7a and 7b show three-dimensional views of another (second) embodiment of the blood pressure measuring system according to the present invention. The same reference signs as in the description of the first embodiment are used for the same components. In the following, in particular the differences in view of the first embodiment are described in more detail.

FIG. 7a shows a view of the second embodiment similar to the view of the first embodiment shown in FIG. 4a. FIG. 7b shows the second embodiment of FIG. 7a in a substantially flat configuration. Only for the sake of clarity, the pressurization means (comprising the pressure actuator 12 with the fluid bag 14) is not illustrated in FIGS. 7a and 7b. However, as will be apparent to those skilled in the art, the pressurization means equally form part of the second embodiment.

As can be seen from FIGS. 7a and 7b, the flexible element 16 of the second embodiment also comprises the evacuation port 16a through which the air-tight pouch of the flexible element 16 can be evacuated thereby stiffening the flexible element 16. The second embodiment also comprises three individually formed shell elements 20a, 20b and 20c of the kinking-proof shell 20 which exhibit a substantially strap-shaped form for surrounding the patient's body part E. However, the second embodiment differs from the first embodiment in that the three individually formed shell elements 20a, 20b and 20c of the kinking-proof shell 20 are each further divided into three sub-elements 20a_1, 20a_2, 20a_3, 20b_1, 20b_2, 20b_3, 20c_1, 20c_2, and 20c_3. Thus, the kinking-proof shell 20 of the second embodiment in total comprises nine shell elements.

The three sub-elements of each of the three shell elements 20a, 20b and 20c are arranged adjacent to each other in a circumferential direction of the body part E when the blood pressure measuring system 10 surrounds the body part E. Furthermore, these adjacent sub-elements are connected to each other by flexible links 21. The shown embodiment, always two adjacent subelements are connected to each other by two flexible links 21. However, another number of flexible hinges may equally be chosen. Even though the links 21 are flexible, they are designed to restrict the maximal bending angle range between two adjacent shell elements. The maximal bending angle range may be restricted to 90°, preferably to 45° or even less. Additionally or alternatively, at least one link 21—preferably each link 21—may comprise a backing member which allows for angles between two adjacent sub-elements smaller than a predetermined maximal angle (e.g. 180°) while at the same time inhibiting any bending angles greater than the predetermined maximal angle.

This way, a shape of the system 10 different from circular, e.g. an elliptic shape, is enabled and mechanical stress in the shell material is reduced, while kinking is still inhibited. In addition, the body part is not forced to a circular cross-section.

Consequently, with the second embodiment, the inventive system 10 is particularly designed to adapt very well to the natural form of the patient's body part E, both in the circumferential direction of the body part E and a direction substantially perpendicular thereto, while inhibiting at the same time the generation of kinks, so that the measurement of the patient's blood pressure can be performed with high accuracy.

FIGS. 8a, 8b and 8c illustrate a further embodiment. The blood pressure measuring system 10 according to the present invention comprises a stiffening kinking-proof shell 30 that is arranged between the body part E and the pressurization means, comprising the fluid bag 14 and a pressure actuator (not shown). The pressure actuator may surround a patient's body part E. The pressure actuator preferably surrounds the fluid bag 14 or is provided in conjunction with the fluid bag

14, wherein the pressure actuator and the fluid bag 14 may form one single component. The kinking-proof shell 30 is arranged between the fluid bag 14 and a textile layer 23, wherein the textile layer 23 is also provided between the fluid bag 14 and the kinking-proof shell 30.

In contrast to the embodiment shown in FIGS. 2a to 7b, the blood pressure measuring system does not exhibit any flexible element providing a stiffening function. Any (additional) flexible element is not required in order to ensure sufficient stiffness of the blood pressure measuring system 10. Sufficient stiffness is exclusively provided by the stiffening kinking-proof shell 30. The stiffening kinking-proof shell 30 exhibits deformation resistance, especially with respect to compression forces.

The kinking-proof shell 30 may be made from plastic material, such as a thermoplastic, e.g. polyethylene (PE). The thickness of the kinking-proof shell 30 is chosen so that the kinking-proof shell 30 does not buckle when pressure is applied to the fluid bag 14. When pressure is applied to the fluid bag 14, overlapping edge regions (i.e., free ends) of the kinking-proof shell may move or slide relatively to each other so as to reduce the diameter of the kinking-proof shell 30. Thereby, the kinking-proof shell 30 may remain substantially ring-shaped, or the kinking-proof shell 30 may take on an at least slightly conical or tapering shape. The dimensional stability of the kinking-proof shell 30 may ensure that any pressure applied by the fluid bag 14 acts on the body part E.

As described in conjunction with FIGS. 2a, 2b, the kinking-proof shell 30 enables reducing the formation of wrinkles or kinks in the compression acting surface of the fluid bag.

FIG. 8c illustrates the textile layer 23 in more detail. The textile layer covers both an inner lateral surface and an outer lateral surface of the kinking-proof shell 30, wherein an overlapping portion of the kinking-proof shell 30 is shown. The textile layer 23 is arranged between the fluid bag 1 and the kinking-proof shell 30, and the textile layer 23 is arranged between the kinking-proof shell 30 and the body part E, too. Thus, any friction due to relative motion between the kinking-proof shell 30 and the body part E or the fluid bag 14 may be minimized. The textile layer 23 surrounds both sides of the kinking-proof shell 30 in a socklike manner, i.e. like a stocking.

A cross-sectional view of the blood pressure measuring system 10 according to FIG. 8b is shown in FIG. 9. The kinking-proof shell 30 comprises one single component. The kinking-proof shell 30 is provided in the form of a one-piece shell. The blood pressure measuring system comprises a pressure transducer 18a which forms part of a pressure sensor unit (not explicitly shown). For example, the pressure transducer 18a may be provided in the form of a pressure-sensitive film, foil or sheet, or in conjunction with a gel or oil cushion (not shown). The pressure transducer 18a is arranged between the kinking-proof shell 30 and the body part E. More particularly, as shown in FIG. 9, the pressure transducer 18a is arranged on an inner lateral surface of the kinking-proof shell 30 and is covered by the textile layer 23. The kinking-proof shell 30 provides a surface on which the pressure transducer 18a can be fixed.

The pressure transducer 18a may be electrically connected to any logic unit of the pressure sensor unit, especially in case the pressure transducer 18a is arranged internally. Alternatively, the pressure transducer 18a may be hydraulically connected to any logic unit of the pressure sensor unit, especially in case the pressure transducer 18a is arranged externally. The connection may be provided e.g. by a tube.

In FIG. 9, an overlapping portion of the kinking-proof shell 30 is shown. The kinking-proof shell 30 only overlaps on one side (of the body part E). The pressure transducer 18a is arranged on the other side, i.e. at a section or portion which does not overlap.

In FIG. 10, a section of one specific embodiment of a stiffening kinking-proof shell 30 is schematically shown. The kinking-proof shell 30 exhibits an inner lateral surface 30.1 and an outer lateral surface 30.3. The kinking-proof shell 30 exhibits a free end 30.2 which may be shaped or angled with an angle a, wherein the angle a preferably is in the range of 40° and 1 35°, more preferably in the range of 70° and 110°, e.g. 105°. Such an angle may ensure that the free end 30.2 does not block at the opposing free end or at any grooves when the overlapping portions begin to move or slide relatively to each other in order to reduce the diameter of the kinking-proof shell.

The kinking-proof shell exhibits wedge-shaped grooves 30.4 which segment both the inner lateral surface 30.1 and the outer lateral surface 30.3 in adjacent shell sections 30.1 a, 30.3a. The grooves have a depth which is lower than factor ⅓ of the wall thickness of the kinking-proof shell.

A pressure transducer 18a is provided in conjunction with the kinking-proof shell 30. The pressure transducer 18a, especially its relative position with respect to the kinking-proof shell 30, is shown only schematically. The pressure transducer 18a may extend in a circumferential direction of the kinking-proof shell 30, especially along a section of at least factor ⅓ or ½ of the absolute measurement of the kinking-proof shell in the circumferential direction, as illustrated by the dotted lines.

IT FOLLOWS A LIST OF EXAMPLES

1. Blood pressure measuring system (10) configured to surround a patient's body part (E), comprising pressurization means (12, 14) for applying pressure to the body part (E), and comprising a kinking-proof shell (20; 30), characterized in that the kinking-proof shell (20; 30) is arranged so as to be located between the pressurization means (12, 14) and the body part (E), when the blood pressure measuring system (10) surrounds the body part (E).

2. Blood pressure measuring system (10) according to example 1, wherein the pressurization means (12, 14) comprises a pressure actuator (12) with a fluid bag (14).

3. Blood pressure measuring system (10) according to example 1 or 2, wherein the kinking-proof shell (20; 30) is dimensioned so as to overlap when surrounding the body part (E).

4. Blood pressure measuring system (10) according to any one of the preceding examples, wherein the kinking-proof shell (30) is a stiffening component which is configured for ensuring stiffness of the blood pressure measuring system (10) for pressure measurement, especially by interaction with the pressurization means (12, 14).

5. Blood pressure measuring system (10) according to any one of the preceding examples, wherein the kinking-proof shell (30) is a two-functions component which is configured to provide both buckling strength and deformation resistance, especially with respect to compression forces.

6. Blood pressure measuring system (10) according to any one of the preceding examples, wherein the kinking-proof shell (30) exhibits a surface, especially an inner lateral surface (30.1), which provides a seating for a pressure transducer (18*a*) and/or a pressure sensor pad.

7. Blood pressure measuring system (10) according to any one of the preceding examples, wherein the kinking-proof shell (30) is a stiffening one-piece shell.

8. Blood pressure measuring system (10) according to any one of the preceding examples, wherein the kinking-proof shell (30) exhibits a free end (30.2) having an angled front side, wherein the front side preferably exhibits two adjacent surface portions which are arranged at an angle in the range of 40° to 135° with respect to each other, preferably in the range of 60° to 120°, more preferably 70° to 110°, and/or wherein the kinking-proof shell (30) exhibits a free end (30.2) having a tapering, preferably a continuously decreasing thickness.

9. Blood pressure measuring system (10) according to any one of the preceding examples, wherein the blood pressure measuring system (10), especially the kinking-proof shell (20; 30), is designed so that overlapping portions thereof can easily slide relatively to each other.

10. Blood pressure measuring system (10) according to any one of the preceding examples, wherein the blood pressure measuring system (10) exhibits a textile layer (23) or textile-like layer which is arranged so as to be located between the kinking-proof shell (20; 30) and the body part (E), wherein the textile layer (23) preferably is provided at least on an inner side, especially an inner lateral surface, of the kinking-proof shell (20; 30).

11. Blood pressure measuring system (10) according to example 10, wherein the textile layer (23) is made of a multifilament, wherein the material of the textile layer (23) preferably is polyamide, wherein the textile layer (23) preferably exhibits a mass per meter in the range between 0.1 and 15 g/1000 m, preferably between 0.3 and 10 g/1000 m, further preferred between 1 and 5 g/1000 m, especially 2 g/1000 m.

12. Blood pressure measuring system (10) according to any of the preceding examples, wherein the kinking-proof shell (20; 30) exhibits a slide coating or surface finishing which allows for a friction coefficient of less than 0.5, preferably of less than 0.3, more preferably of less than 0.2, and even more preferably of less than 0.1, at least in overlapping surface portions.

13. Blood pressure measuring system (10) according to any one of the preceding examples, wherein the kinking-proof shell (20; 30) is made from metal and/or plastic, in particular fiber-reinforced plastic, wherein the kinking-proof shell (20; 30) is preferably made from or coated with a thermoplastic material, more preferably made from polyurethane or a polyolefin, even more preferably made from polyethylene and/or polytetrafluorethylene or coated with polytetrafluoroethylene.

14. Blood pressure measuring system (10) according to any one of the preceding examples, wherein the kinking-proof shell (20; 30) exhibits a thickness of between about 0.25 mm and about 6 mm, preferably between about 1 mm and about 3 mm, more preferably between about 1.0 mm and about 2.0 mm, wherein the kinking-proof shell (20; 30) is preferably substantially made from plastic material.

15. Blood pressure measuring system (10) according to any one of the preceding examples, wherein the kinking-proof shell (20; 30) exhibits a modulus of elasticity of more than 50 MPa, preferably of between about 100 MPa and about 10 GPa, more preferably of between about 200 MPa and about 1 GPa.

16. Blood pressure measuring system (10) according to any one of the preceding examples, wherein the kinking-proof shell (20; 30) exhibits a substantially cylindrical or, preferably, conical configuration.

17. Blood pressure measuring system (10) according to any one of the preceding examples, wherein the kinking-proof shell (20; 30) comprises a plurality of individual shell elements (20*a*, 20*b*, 20*c*; 20*a*_1, 20*a*_2, 20*a*_3, 20*b*_1, 20*b*_2, 20*b*_3, 20*c*_1, 20*c*_2, 20*c*_3) or shell sections (30.1 *a*, 30.3*a*).

18. Blood pressure measuring system (10) according to example 17, wherein at least two elements or sections (30.1 *a*, 30.3*a*) of the plurality of individual shell elements (20*a*, 20*b*, 20*c*; 20*a*_1, 20*a*_2, 20*a*_3, 20*b*_1, 20*b*_2, 20*b*_3, 20*c*_1, 20*c*_2, 20*c*_3) or shell sections (30.1 *a*, 30.3*a*) are arranged substantially parallel to each other, each extending in a circumferential direction of the body part (E) when the blood pressure measuring system (10) surrounds the body part (E).

19. Blood pressure measuring system (10) according to example 17 or 18, wherein at least two elements or sections of the plurality of individual shell elements (20*a*_1, 20*a*_2, 20*a*_3, 20*b*_1, 20*b*_2, 20*b*_3, 20*c*_1, 20*c*_2, 20*c*_3) or shell sections (30.1 *a*, 30.3*a*) are arranged adjacent to each other in a circumferential direction of the body part (E) when the blood pressure measuring system (10) surrounds the body part (E).

20. Blood pressure measuring system (10) according to any of examples 17 to 19, wherein at least two sections of the plurality of individual shell sections (30.1 *a*, 30.3*a*) are separated from each other by a groove (30.4), the groove preferably being wedge-shaped.

21. Blood pressure measuring system (10) according to any one of the preceding examples, further comprising a pressure sensor unit, wherein the pressure sensor unit is preferably arranged so as to be at least partially located between the kinking-proof shell (20; 30) and the body part (E), more preferably next to the body part (E), when the blood pressure measuring system (10) surrounds the body part (E).

22. Blood pressure measuring system (10) according to example 21, wherein the pressure sensor unit comprises a pressure transducer (18*a*) or pressure sensor pad which is arranged at an inner side or on an inner lateral surface (30.1) of the kinking-proof shell (30), especially between the inner lateral surface (30.1) and a/the textile layer (23) covering the inner lateral surface (30.1).

23. Blood pressure measuring system (10) according to example 22, wherein the pressure transducer (18*a*) or pressure sensor pad extends in a circumferential direction of the kinking-proof shell (30) when the blood pressure measuring system (10) surrounds the body part (E), especially along a section of at least factor ⅓ or ¼ of the absolute measurement of the kinking-proof shell (30) in the circumferential direction.

24. Blood pressure measuring system (10) according to any one of the preceding examples, wherein at least the pressurization means (12, 14) and the kinking-proof shell (20; 30), preferably all components of the system (10), are connected to each other in such a way as to form a single unit.

25. Method of applying a blood pressure measuring system (10) configured to surround a patient's body part (E), especially a blood pressure measuring system (10) according to any of the preceding examples, comprising the steps:

providing a kinking-proof shell (20; 30) around the body part (E) between pressurization means (12, 14) and the body part (E), applying pressure to the pressurization means (12, 14), and pressing the kinking-proof shell (20; 30) against the body part (E).

26. Method according to example 25, wherein the blood pressure measuring system (10) is stiffened by pressing the kinking-proof shell (30) against the body part (E).

The invention claimed is:

1. A blood pressure measuring system configured to surround a body part, comprising:

a pressurizer configured to apply pressure to the body part;

a pressure sensor unit including a gel or oil cushion and a pressure transducer located in or on the gel or oil cushion;

a kinking-proof shell configured for placement between the pressurizer and the body part when the blood pressure measuring system surrounds the body part, the kinking-proof shell having overlapping portions that are slidable relative to each other for reducing an inner diameter of the kinking-proof shell when pressure is applied to the pressurizer, but the kinking-proof shell having rigidity that prevents buckling of the kinking-proof shell when the pressure is applied by the pressurizer, wherein the kinking-proof shell includes a surface to which the pressure sensor unit is fixed, the pressure sensor unit arranged so as to be at least partially located between the kinking-proof shell and the body part; and a textile layer between:

an inner lateral surface of the kinking-proof shell and the body part, at least a part of the textile layer configured for placement against the body part; and an outer lateral surface of the kinking-proof shell and the pressurizer.

2. The blood pressure measuring system according to claim 1, wherein the pressurizer comprises a pressure actuator with a fluid bag.

3. The blood pressure measuring system according to claim 1, wherein the kinking-proof shell is configured for ensuring stiffness of the blood pressure measuring system for pressure measurement.

4. The blood pressure measuring system according to claim 1, wherein the kinking-proof shell is a two-functions component which is configured to provide both buckling strength and de-formation resistance.

5. The blood pressure measuring system according to claim 1, wherein the kinking-proof shell is a stiffening two-piece shell, and wherein the kinking-proof shell is made from metal or plastic.

6. The blood pressure measuring system according to claim 1, wherein the kinking-proof shell exhibits a free end having an angled front side, wherein the front side preferably exhibits two adjacent surface portions which are arranged at an angle in the range of 40° to 135° with respect to each other.

7. The blood pressure measuring system according to claim 1, wherein the textile layer is made of a multifilament, wherein the textile layer preferably exhibits a mass per meter in the range between 0.1 and 15 g/1000 m.

8. The blood pressure measuring system according to claim 1, wherein the kinking-proof shell exhibits a slide coating or surface finishing which allows for a friction coefficient of less than 0.5 at least in overlapping surface portions.

9. The blood pressure measuring system according to claim 1, wherein the kinking-proof shell exhibits a thickness of between about 0.25 mm and about 6 mm.

10. The blood pressure measuring system according to claim 1, wherein the kinking-proof shell exhibits a modulus of elasticity of more than 50 MPa.

11. The blood pressure measuring system according to claim 1, wherein the kinking-proof shell exhibits a substantially cylindrical or conical configuration.

12. The blood pressure measuring system according to claim 1, wherein the kinking-proof shell comprises a plurality of individual shell sections.

13. The blood pressure measuring system according to claim 12, wherein at least two sections of the plurality of individual shell sections are arranged parallel to each other, each extending in a circumferential direction of the body part when the blood pressure measuring system surrounds the body part.

14. The blood pressure measuring system according to claim 12, wherein at least two sections of the plurality of individual shell sections are arranged adjacent to each other in a circumferential direction of the body part when the blood pressure measuring system surrounds the body part.

15. The blood pressure measuring system according to claim 12, wherein at least two sections of the plurality of individual shell sections are separated from each other by a groove, the groove preferably being wedge-shaped.

16. The blood pressure measuring system according to claim 1, wherein at least the pressurizer and the kinking proof shell connected to each other in such a way as to form a single unit.

17. The blood pressure measuring system according to claim 1, wherein the textile layer surrounds the kinking-proof shell.

18. The blood pressure measuring system according to claim 1, wherein the pressure transducer is arranged at an inner side or an inner lateral surface of the kinking-proof shell and extends in a circumferential direction of the kinking-proof shell when the blood pressure measuring system surrounds the body part.

19. The blood pressure measuring system according to claim 1, wherein the gel or oil cushion is configured to be in direct contact with the body part.

\* \* \* \* \*